United States Patent [19]

Brunetti et al.

[11] 4,191,683

[45] Mar. 4, 1980

[54] DERIVATIVES OF 4-AMINOPIPERIDINE AS STABILIZERS FOR POLYMERS

[75] Inventors: Heimo Brunetti, Reinach; Jean Rody, Basel, both of Switzerland; Nobuo Soma; Tomoyuki Kurumada, both of Tokyo, Japan

[73] Assignees: Ciba-Geigy Corporation, Ardsley, N.Y.; Sankyo Company Limited, Tokyo, Japan

[21] Appl. No.: 853,658

[22] Filed: Nov. 21, 1977

Related U.S. Application Data

[63] Continuation-in-part of Ser. No. 687,826, May 19, 1976, abandoned.

[30] Foreign Application Priority Data

May 28, 1975 [GB] United Kingdom ............... 23226/75

[51] Int. Cl.$^2$ ...................... C08K 5/34; C07D 211/56; C07D 211/92
[52] U.S. Cl. ............................. 260/45.8 N; 106/124; 106/176; 252/403; 542/417; 544/130; 544/198; 544/209; 544/212; 546/189; 546/190; 546/223; 546/224
[58] Field of Search ...................... 260/45.8 N, 293.51, 260/293.61, 293.63, 293.64, 293.71, 293.73, 293.74, 293.76, 293.77, 293.81, 293.82, 293.84, 293.85, 293.86, 293.88, 293.9; 542/417; 544/130, 198, 209, 212

[56] References Cited

U.S. PATENT DOCUMENTS

| | | | |
|---|---|---|---|
| 3,147,268 | 9/1964 | Meltzer et al. ................... | 260/293.86 |
| 3,225,037 | 12/1965 | Zenitz et al. ..................... | 260/293.86 |
| 3,311,624 | 3/1967 | Ohnacker et al. ............... | 260/293.67 |
| 3,371,093 | 2/1968 | Zenitz et al. ..................... | 260/293.71 |
| 3,513,170 | 5/1970 | Murayama et al. .............. | 260/294.7 |
| 3,534,048 | 10/1970 | Murayama et al. ............. | 260/293.71 |
| 3,684,765 | 8/1972 | Matsui et al. .................... | 260/45.8 N |
| 3,705,166 | 12/1972 | Murayama et al. ............. | 260/45.8 N |
| 3,904,581 | 9/1975 | Murayama et al. ............. | 260/45.8 N |
| 3,910,932 | 10/1975 | Cavalla et al. ................... | 260/293.69 |
| 3,925,376 | 12/1975 | Chalmers et al. ............. | 260/248 CS |
| 3,933,832 | 1/1976 | Langbein et al. ............... | 260/293.69 |
| 4,148,783 | 4/1979 | Rasberger et al. ............. | 260/45.8 N |

OTHER PUBLICATIONS

DOS 2040975, Matsui et al (Sanky Co. Ltd) Feb. 10, 1972.
Ranby et al. Photodegradation, Photooxidation and Photostabilization of Polymers, Wiley & Sons, 1975, pp. 392-395.
Modern Plastics Encyclopedia, 1969/70, p. 308; 1970/71, p. 410; 1973/74, p. 271; and 1974/75, pp. 104/105.
Mascia, The Role of Additives in Plastics, Edward Arnold, 1974, pp. 2-7.
Skeist Laboratories, Information Folder, p. 321.
Thinius, Stabilisierung und Stabilisatoren von Plastwerkstoffen, Verlag Chemie 1969, pp. 80-83.
Domininghaus, Zusatzstoffe fur Kunststoffe, Zechner & Huthig, 1978, pp. 10/11.

*Primary Examiner*—H. S. Cockeram
*Attorney, Agent, or Firm*—Vincent J. Cavalieri

[57] ABSTRACT

Derivatives of sterically hindered 4-aminopiperidines are effective as light-stabilizers for organic polymers, especially for polyolefins. The piperidine ring is substituted with at least five alkyl groups, preferably methyl and ethyl groups. The 4-amino group is substituted with mono- or divalent acyl groups. The nitrogen in 1-position may also be substituted with a monovalent organic substituent. The compounds can be synthesized starting from higher homologs of acetone in sequence of several reaction steps.

13 Claims, No Drawings

DERIVATIVES OF 4-AMINOPIPERIDINE AS STABILIZERS FOR POLYMERS

This application is a continuation-in-part application of co-pending U.S. patent application Ser. No. 687,826, filed May 19, 1976 and now abandoned.

This invention relates to new derivatives of 4-aminopiperidine and their use as stabilizers for organic polymers against light-induced deterioration.

In the U.S. Pat. No. 3,684,765 there is disclosed the stabilisation of polymers by incorporating stabilizers which are derivatives of 4-aminopiperidine. More particularly these stabilizers are derivatives of 4-amino-2,2,6,6-tetramethylpiperidine having the formula

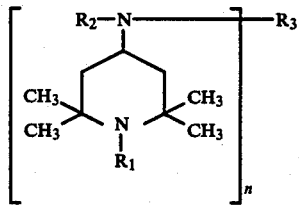

wherein $R_1$ represents hydrogen or an acyl group; $R_2$ represents hydrogen or a monovalent hydrocarbon residue; $R_3$ represents hydrogen, an alkoxycarbonyl group or a mono-, di- or trivalent acyl, carbamoyl or thiocarbamoyl group.

Similar derivatives of 4-amino-2,2-dimethylpiperidine are disclosed in the German OS No. 2 349 962 dealing with the stabilisation of polymers.

Derivatives of 4-amino-2,2,6,6-tetraalkylpiperidines having alkyl groups higher than methyl in 2-position and alkyl groups in 3-position of the piperidine ring have not hitherto become known.

It has been found now that such higher alkylated 4-aminopiperidine derivatives are valuable stabilizers for organic polymers normally subject to deterioration by light. The new higher alkylated 4-aminopiperidine derivatives are defined by the formula I

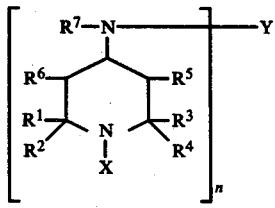

(I)

or mixtures of isomers thereof or acid addition salts thereof, wherein $R^1$ and $R^3$ are each ethyl,
$R^2$ and $R^4$ are each methyl,
$R^5$ is methyl and
$R^6$ is hydrogen whereby $R^5$ and $R^6$ are interchangeable, X is hydrogen, an oxyl radical, alkyl having 1 to 8 C-atoms, alkenyl having 3 to 8 C-atoms, aralkyl having 7 or 8 carbon atoms, an aliphatic acyl group having 7 to 12 C-atoms, or one of the groups $—CH_2COOR^8$, $—CH_2CH(R^9)—OH$ and $—CONHR^{10}$, $R^7$ is hydrogen, alkyl having 1 to 12 C-atoms, cycloalkyl having 5 to 7 C-atoms or aralkyl having 7 or 8 C-atoms, and, if n is 2 and Y is alkylene having 2 to 10 C-atoms, 2-butenylene, arylene having 6 to 12 C-atoms, meta- or para-xylylene or 1,4-cyclohexylene, $R^7$ is hydrogen, a group $—CO—R^{11}$ or a group $—CO—R^{12}—COOH$, $R^8$ is alkyl having 1 to 8 C-atoms or phenyl,
$R^9$ is hydrogen, methyl or phenyl,
$R^{10}$ is alkyl having 1 to 12 C-atoms, phenyl or cyclohexyl,
$R^{11}$ is hydrogen, alkyl having 1 to 17 carbon atoms, alkenyl having 2 to 5 C-atoms, alkoxy having 1 to 8 C-atoms or phenyl,
$R^{12}$ is

$—CH=CH—$, $—(CH_2)_3$, o-phenylene or o-cyclohexylene, n is 1, 2 or 3,

Y, if n is 1, represents hydrogen, $—CH_2CH_2OH$, a group $—CO—R^{13}$,

$—SO_2—R^{16}$, $—CO—R^{12}—COOH$, $—CO—R^{12}—COOMe$ or

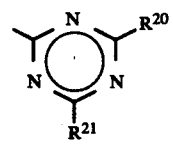

Y and $R^7$ together with the N-atom to which they are attached form a succinimide ring which is unsubstituted or substituted by alkyl having 1 to 12 carbon atoms, a maleimide, dimethylmaleimide, phthalimide, tetrahydrophthalimide or hexahydrophthalimide ring, and, if n is 2, Y represents $—CO—$, $—CO—CO—$, $—CO—R^{18}—CO—$, $—CONH—R^{19}—NHCO—$ or

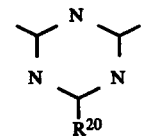

$R^{13}$ is hydrogen, alkyl having 1 to 17 C-atoms, alkenyl having 2 to 5 carbon atoms, alkoxy having 1 to 8 C-atoms, benzyloxy, cyclohexyloxy, cycloalkyl having 5 to 7 C-atoms, phenyl unsubstituted or substituted by alkyl having 1 to 4 C-atoms, $R^{14}$ is hydrogen or alkyl having 1 to 4 C-atoms,
$R^{15}$ is hydrogen, alkyl having 1 to 18 C-atoms, aryl having 6 to 10 C-atoms, aralkyl having 7 or 8 C-atoms or cyclohexyl or $R^{14}$ and $R^{15}$ together with the N-atom to which they are attached may form a piperidine, pyrrolidine or morpholine ring, $R^{16}$ is methyl, ethyl, phenyl or methylphenyl,
$R^{17}$ is hydrogen or alkyl having 1 to 12 C-atoms,
Me is the equivalent of a salt-forming mono- to tetravalent metal kation, $R^{18}$ is alkylene having 1 to 10 C-atoms, alkenylene having 2 to 4 C-atoms, arylene having 6 to 12 C-atoms or cyclohexylene, $R^{19}$ is alkylene having 2 to 10 C-atoms, arylene having 6 to 13 C-atoms or cyclohexylene, $R^{20}$ and $R^{21}$ are the same or different, and represent a chlorine atom, $—N(R^{22})R^{23}$, $—NH—R^{24}$ or $—OR^{17}$, wherein $R^{17}$ has the meaning given above, $R^{22}$ and $R^{23}$ are the same or different, and represent hydrogen, alkyl having 1 to 18 carbon atoms, alkyl which is substituted by one hydroxy, alkoxy or cyano group and which has up to 21 C-atoms; alkenyl having 3 or 4 C-atoms or cyclohexyl having 5 to 18 C-atoms, $R^{24}$ is phenyl unsubstituted or substituted by one —OH and/or 1 or 2 alkyl groups each having 1 to 5 C-atoms, and, if $R^7$ is hydrogen or a group $—CO—R^{11}$, Y may also be alkylene having 2 to 10 C-atoms, 2-butenylene, arylene having 6 to 12 C-atoms, meta- or para-xylylene or 1,4-cyclohexylene, and, if n is 3, Y is the 1,3,5-triazine-2,4,6-triyl residue.

When $R^7$ is alkyl having up to 12 C-atoms this may preferably be a straight-chain alkyl group, such as methyl, ethyl, propyl, n-butyl, n-pentyl, n-hexyl, n-decyl or n-dodecyl. When $R^7$ is aralkyl it may be benzyl, phenylethyl or methylbenzyl, preferably benzyl. When $R^7$ is cycloalkyl it may be cyclopentyl, cyclohexyl or a methyl derivative thereof; preferably it may be cyclohexyl. Most preferably $R^7$ is hydrogen.

When $R^7$ is a group $—CO—R^{11}$, $R^{11}$ may be hydrogen, an alkyl group having from 1 to 17 carbon atoms, e.g., methyl, ethyl, n- or isopropyl, n- or tert.butyl, n- or isopentyl, 1-ethyl-pentyl, nonyl, undecyl, pentadecyl or heptadecyl; an alkenyl group having from 2 to 5 carbon atoms, e.g., vinyl, 1-propenyl, 2-methyl-1-propenyl, isopropenyl or 1,3-pentadienyl; an alkoxy group having 1 to 8 carbon atoms such as methoxy, ethoxy, butoxy or octoxy; or a phenyl group.

Preferred groups $—CO—R^{11}$ are those wherein $R^{11}$ is hydrogen or alkyl having 1 to 4 carbon atoms.

If $R^7$ and/or Y is a group $—CO—R^{12}—COOH$, this may be

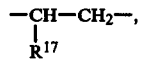

$—CH=CH—$, $—(CH_2)_3$, ortho-phenylene or ortho-cyclohexylene, $R^{17}$ being hydrogen or a straight or branched alkyl group having 1 to 12 carbon atoms, such as those listed under $R^{11}$. $R^{12}$ preferably represents $—(CH_2)_3$, and, particularly, $—(CH_2)_2$, $—CH=CH—$ or ortho-phenylene.

When X is an alkyl group having from 1 to 8 carbon atoms it may be e.g., methyl, ethyl, n-propyl, n-butyl, n-hexyl or n-octyl, especially an alkyl group having from 1 to 4 carbon atoms and most preferably methyl.

When X is an alkenyl group having 3 to 8 and preferably from 3 to 6 carbon atoms it may be e.g., allyl, 2-butenyl, 2-hexenyl or 2-octenyl, especially an alkenyl group having 3 or 4 carbon atoms, and most preferably allyl.

When X is an aralkyl group having 7 or 8 carbon atoms it may be e.g., benzyl, phenylethyl, o-, m- or p-methylbenzyl, especially benzyl.

When X is an aliphatic acyl group having up to 12 carbon atoms, it may be an alkanoyl or an alkenoyl group, e.g., formyl, acetyl, acryloyl, crotonoyl, capryloyl or lauroyl.

When X is a group of the formula $—CH_2—COOR^8$, $R^8$ may be an alkyl group having from 1 to 8 carbon atoms, e.g., methyl, ethyl, isopropyl, n-butyl, isobutyl, tert.butyl, isopentyl or octyl, or a phenyl group, especially an alkyl group from 1 to 4 carbon atoms.

When X is a group of the formula $—CH_2CH(R^9)—OH$, $R^9$ may be a hydrogen atom, a methyl group or a phenyl group, preferably hydrogen.

When X is a group $—CONHR^{10}$, $R^{10}$ may be an alkyl group having from 1 to 12 carbon atoms, e.g., methyl, ethyl, n-propyl, n-butyl, dodecyl or 2-ethylhexyl; a phenyl group or a cyclohexyl group.

When n is 1, Y may be a group $—CO—R^{13}$ wherein $R^{13}$ is hydrogen, an alkyl group having 1 to 17 carbon atoms, an alkenyl group having 2 to 5 carbon atoms or an alkoxy group having 1 to 8 carbon atoms such as those listed under $R^{11}$; a benzyloxy group; a cyclohexyloxy group; a cycloalkyl group having 5–7 carbon atoms, e.g., cyclopentyl, cyclohexyl or methylcyclohexyl; a phenyl group which may optionally be substituted with a $C_{1-4}$ alkyl group, e.g., phenyl, o-, m- or p-methyl-, p-isopropyl or p-tert.butylphenyl.

When Y is a group of the formula

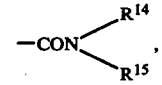

$R^{14}$ may be a hydrogen atom, an alkyl group having from 1 to 4 carbon atoms, (e.g., methyl, ethyl, n-propyl, n-butyl), $R^{15}$ may be hydrogen, an alkyl group having from 1 to 18 carbon atoms, e.g., methyl, ethyl, n-propyl, n-butyl, dodecyl, 2-ethylhexyl, n-hexadecyl or n-octadecyl; an aryl group having from 6 to 10 carbon atoms which may optionally be substituted with chlorine or $C_{1-4}$ alkyl, such as phenyl, o-, m- or p-chlorophenyl, o-, m- or p-tolyl or $\alpha$- or $\beta$-naphthyl; an aralkyl group having from 7 to 8 carbon atoms, e.g., benzyl or phenylethyl; or a cyclohexyl group, or $R^{14}$ and $R^{15}$ together with the nitrogen atom to which they are attached represent a piperidino, a pyrrolidino or a morpholino group.

Particularly preferred are groups $—CONH—R^{15}$ wherein $R^{15}$ is benzyl or cyclohexyl and especially those wherein $R^{15}$ is hydrogen, alkyl having 1 to 18 carbon atoms or phenyl.

When Y is a group $—SO_2—R^{16}$, $R^{16}$ preferably represents methyl, phenyl or methylphenyl, especially para-methylphenyl.

When Y is a group of the formula $—CO—R^{12}—COOMe$, the metal kation Me is the equivalent of a salt-forming metal, e.g., Na, Ba, Ni, Ca, Zn, Co or Sn.

Alkyl substituents or succinimide rings formed by Y and $R^7$ together with the N-atom to which they are attached, have 1 to 12 carbon atoms and may be branched or straight. Such alkyl substituents are preferably straight-chained and have 1 to 4 carbon atoms.

If $R^7$ and Y together form a ring as defined, this is preferably a succinimide, maleimide, dimethylmaleimide or phthalimide ring.

When n=2:

When Y is a diacyl group $—CO—R^{18}—CO—$, $R^{18}$ may be an alkylene group having from 1 to 10 carbon atoms, e.g., methylene, ethylene, tetramethylene, hexamethylene, octamethylene or decamethylene; an alkenylene group having from 2 to 4 carbon atoms, e.g., vinylene, 2-butenylene or

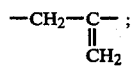

an arylene group having 6–12 carbon atoms, e.g., o-, m- or p-phenylene, 1,4-naphthylene, 4,4'-diphenylene; or a cyclohexylene group.

When Y is a group of the formula —CO—NH—$R^{19}$—NHCO—, $R^{19}$ may be an alkylene group having 2 to 10 carbon atoms, e.g., ethylene, tetramethylene, hexamethylene or decamethylene; an arylene group having from 6 to 13 carbon atoms which may optionally be substituted with methyl, e.g., o-, m- or p-phenylene, 2,4-tolylene, 1,5-naphthylene, 4,4'-diphenylene, 4,4'-diphenylenemethane or 4,4'-diphenylene oxide; or a cyclohexylene group, e.g., 1,4-cyclohexylene.

If Y represents

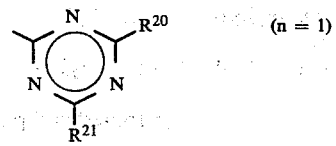

or

and $R^{20}$ and/or $R^{21}$ is a group —N($R^{22}$)$R^{23}$, —NH—$R^{24}$ or —O$R^{17}$, $R^{17}$ may be hydrogen or an alkyl group having 1 to 12 carbon atoms as defined above, $R^{22}$ and/or $R^{23}$ may be straight or branched alkyl having 1 to 18 carbon atoms, preferably hydrogen or alkyl having 6 to 18 carbon atoms, substituted alkyl as defined, alkenyl having 3 or 4 carbon atoms, especially allyl, or cycloalkyl having 5 to 18 and preferably 5 to 12 carbon atoms, such as cyclopentyl, cyclohexyl and cyclododecyl.

Substituted alkyl groups $R^{22}$ and $R^{23}$ as defined may also be branched but are preferably straight-chained. Examples of such substituted alkyl groups are —CH$_2$CH$_2$OH, —CH$_2$CH$_2$CN, —CH$_2$CH$_2$O(CH$_2$)$_3$CH$_3$ and —CH$_2$O(CH$_2$)$_7$CH$_3$.

If one or both of $R^{20}$ and $R^{21}$ represent a group —NH—$R^{24}$, $R^{24}$ may be, e.g., phenyl, o-, m- and p-methylphenyl, p-hydroxyphenyl or 3,5-di-tert-butyl-4-hydroxyphenyl.

If $R^7$ is hydrogen or a group —CO—$R^{11}$, Y may also be an alkylene group having 2–10 C-atoms, e.g., a di-, tri-, tetra-, hexa-, octa- or decamethylene residue; 2-butenylene, or it may be an arylene group having 6 to 12 carbon atoms, such as phenylene, naphthylene or diphenylene; meta- or para-xylylene or 1,4-cyclohexylene.

Acid addition salts of compounds of formula I are also intended to be covered by the scope of the present invention. For example, acids which form such addition salts may be inorganic acids such as sulfuric, hydrochloric or phosphoric acid; organic carboxylic acids such as formic, acetic, valeric, stearic, oxalic, adipic, sebacic, maleic, benzoic, p-tert.butyl-benzoic, 3,5-ditert.-butyl-4-hydroxybenzoic, salicyclic or terephthalic acid; sulfonic acids such as methanesulfonic or p-toluenesulfonic acid: or organic phosphorus acids such as diphenyl phosphoric acid or phenyl phosphonic acid.

The 4-aminopiperidine derivatives having the aforementioned general formula I possess asymmetric carbon atoms. Accordingly, by the term "mixtures of isomers thereof" are meant not only mixtures of position isomers at 3- and 5- position but also various kinds of stereo isomers. At any stage of the synthesis of the compounds according to the invention, the mixture of isomers usually obtained in the preparation of the corresponding 4-piperidinone derivative which is used as starting material, can be separated by methods known per se.

Preferred compounds of formula I are those wherein
X is hydrogen, an oxyl radical, alkyl having 1 to 8 C-atoms, alkenyl having 3 or 4 carbon atoms, benzyl, an aliphatic acyl group having 1 to 4 carbon atoms, or —CH$_2$CH$_2$OH, $R^7$ is hydrogen, alkyl having 1 to 12 carbon atoms, cyclohexyl or benzyl, and, if n is 2 and Y is alkylene having 2 to 10 carbon atoms, $R^7$ is hydrogen or a group —CO—$R^{11}$ wherein $R^{11}$ is hydrogen or alkyl having 1 to 4 carbon atoms, Y, if n is 1, represents hydrogen, a group —CO—$R^{13}$, —CO—NH—$R^{15}$, —SO$_2R^{16}$ or —CO—$R^{12}$—COOH, or Y and $R^7$ together with the N-atom to which they are attached form a succinimide, maleimide, dimethylmaleimide or phthalimide ring, and, if n is 2, Y represents —CO—, —CO—CO—, —CO—$R^{18}$—CO— or —CONH—$R^{19}$—NHCO—, $R^{12}$ is —(CH$_2$)$_2$—, —(CH$_2$)$_3$—, —CH=CH— or o-phenylene, $R^{13}$ is hydrogen, alkyl having 1 to 11 C-atoms, alkenyl having 2 to 3 C-atoms, alkoxy having 1 to 8 C-atoms or phenyl, $R^{15}$ is hydrogen, alkyl having 1 to 18 C-atoms, phenyl, benzyl or cyclohexyl, $R^{16}$ is methyl, phenyl or methylphenyl, $R^{18}$ is alkylene having 1 to 10 C-atoms or phenylene, $R^{19}$ is alkylene having 2 to 10 C-atoms or arylene having 6 or 7 C-atoms, and, if $R^7$ is hydrogen or a group —CO—$R^{11}$, Y may also be alkylene having 2 to 10 C-atoms, and, if n is 3, Y is the 1,3,5-triazine-2,4,6-triyl residue.

Particularly preferred are compounds of formula I wherein X is hydrogen, methyl, benzyl, aliphatic acyl having 1 to 4 carbon atoms or 2-hydroxyethyl, $R^7$ is hydrogen, alkyl having 1 to 12 carbon atoms, benzyl, or, if n is 2 and Y is alkylene having 2 to 10 carbon atoms, $R^7$ is hydrogen or acetyl, Y, if n is 1, represents hydrogen, —CH$_2$CH$_2$OH, —CO—$R^{13}$ wherein $R^{13}$ is hydrogen, alkyl having 1 to 7 carbon atoms, alkenyl having 2 or 3 carbon atoms or phenyl, —CONH—$R^{15}$ wherein $R^{15}$ is alkyl having 1 to 18 carbon atoms or phenyl, —SO$_2R^{16}$ wherein $R^{16}$ is methyl, phenyl or para-methylphenyl, —CO—$R^{12}$—COOH wherein $R^{12}$ is —CH$_2$CH$_2$—, —CH=CH— or o-phenylene, or Y and $R^7$ together with the N-atom to which they are attached form a succinimide, maleimide or phthalimide ring, if n is 2, Y represents —CO—, —CO—CO—, —CO—$R^{18}$—CO— wherein $R^{18}$ is alkylene having 1 to 8 carbon atoms or phenylene or —CONH—$R^{19}$—NH- CO— wherein $R^{19}$ is alkylene having 2 to 6 carbon atoms or tolylene, and if $R^7$ is hydrogen or acetyl, Y may also be alkylene having 2 to 6 carbon atoms, and, if n is 3, Y represents the 1,3,5-triazine-2,4,6-triyl residue, and especially those wherein $R^7$ is hydrogen, alkyl having 1 to 12 carbon atoms or benzyl, X is hydrogen or methyl and Y is hydrogen when n=1, or, if n=2 and $R^7$ is hydrogen or acetyl, Y is alkylene having 2 to 6 carbon atoms.

The following is a list of individual 4-amino-piperidine derivatives of formula I. It is, however, to be understood that the present invention is not limited to these illustrating compounds.

4-acetamido-2,6-diethyl-2,3,6-trimethylpiperidine
4-lauroylamido-2,6-diethyl-2,3,6-trimethylpiperidine
4-stearamido-2,6-diethyl-2,3,6-trimethylpiperidine
4-acrylamido-2,6-diethyl-2,3,6-trimethylpiperidine
4-methacrylamido-2,6-diethyl-2,3,6-trimethylpiperidine
4-crotonamido-2,6-diethyl-2,3,6-trimethylpiperidine
4-phenylacetamido-2,6-diethyl-2,3,6-trimethylpiperidine
4-cyclohexanecarbonamido-2,6-diethyl-2,3,6-trimethylpiperidine
4-benzamido-2,6-diethyl-2,3,6-trimethylpiperidine
4-benzamido-2,6-diethyl-1,2,3,6-tetramethylpiperidine
4-benzamido-2,6-diethyl-2,3,6-trimethylpiperidine-1-oxyl
4-p-toluamido-2,6-diethyl-1,2,3,6-trimethylpiperidine
2(2,6-deithyl-2,3,6-trimethylpiperidyl-4-amino)-4-chloro-6-ethylamino-1,3,5-triazine
4-o-toluamido-2,6-diethyl-2,3,6-trimethylpiperidine
4-β-naphthamido-2,6-diethyl-2,3,6-trimethylpiperidine
4-ureido-2,6-diethyl-2,3,6-trimethylpiperidine
4(3-ethylureido)-2,6-diethyl-2,3,6-trimethylpiperidine
4-(3-benzylureido)-2,6-diethyl-2,3,6-trimethylpiperidine
4-(3-cyclohexylureido)-2,6-diethyl-2,3,6-trimethylpiperidine
4-(3-phenylureido)-2,6-diethyl-2,3,6-trimethylpiperidine
4-(3-phenylureido)-2,6-diethyl-1,2,3,6-tetramethylpiperidine
4-(3-stearylureido)-2,6-diethyl-2,3,6-trimethylpiperidine
4-(3,3-dimethylureido)-2,6-diethyl-2,3,6-trimethylpiperidine
4-methansulfonamido-2,6-diethyl-2,3,6-trimethylpiperidine
4-benzenesulfonamido-2,6-diethyl-2,3,6-trimethylpiperidine
4-p-toluenesulfonamido-2,6-diethyl-2,3,6-trimethylpiperidine
4-amino-2,6-diethyl-2,3,6-trimethylpiperidine
4-methylamino-2,6-diethyl-2,3,6-trimethylpiperidine
4-caprylamido-2,6-diethyl-2,3,6-trimethylpiperidine
4-cyclohexylamino-2,6-diethyl-2,3,6-trimethylpiperidine
4-benzylamino-2,6-diethyl-2,3,6-trimethylpiperidine
4-(N-methylacetamido)-2,6-diethyl-2,3,6-trimethylpiperidine
4-(N-methylbenzamido)-2,6-diethyl-2,3,6-trimethylpiperidine
4-(N-cyclohexylbenzamido)-2,6-diethyl-2,3,6-trimethylpiperidine
4-(N-benzylbenzamido)-2,6-diethyl-2,3,6-trimethylpiperidine
4-acetamido-1-butyl-2,6-diethyl-2,3,6-trimethylpiperidine
4-benzamido-1-allyl-2,6-diethyl-2,3,6-trimethylpiperidine
4-acetamido-1-benzyl-2,6-diethyl-2,3,6-trimethylpiperidine
1,3-bis(2,6-diethyl-2,3,6-trimethyl-4-piperidyl)urea
N,N'-bis(2,6-diethyl-2,3,6-trimethyl-4-piperidyl)oxalamide
N,N'-bis(2,6-diethyl-1,2,3,6-tetramethyl-4-piperidyl)oxalamide
2,4-bis(2,6-diethyl-2,3,6-trimethylpiperidyl-4-amino)-6-phenylamino-1,3,5-triazine
N,N'-bis(2,6-diethyl-2,3,6-trimethyl-4-piperidyl)succinamide
N,N'-bis(2,6-diethyl-2,3,6-trimethyl-4-piperidyl)adipamide
N,N'-bis(2,6-diethyl-2,3,6-trimethyl-4-piperidyl)sebacamide
N,N'-bis(2,6-diethyl-2,3,6-trimethyl-4-piperdyl)fumaramide
N,N'-bis(2,6-diethyl-2,3,6-trimethyl-4-piperidyl)terephthalamide
1,6-bis[3-(2,6-diethyl-2,3,6-trimethyl-4-piperidyl)ureido]-n-hexane
p,p'-bis[3-(2,6-diethyl-2,3,6-trimethyl-4-piperidyl)ureido]-diphenylmethan
2,4-bis[3-(2,6-diethyl-2,3,6-trimethyl-4-piperidyl)ureido]-toluene
1,5-bis[3-(2,6-diethyl-2,3,6-trimethyl-4-piperidyl)ureido]-naphthalene
p,p'-bis[3-(2,6-diethyl-2,3,6-trimethyl-4-piperidyl)ureido]-diphenyloxide
1,6-bis[3-(2,6-diethyl-1,2,3,6-tetramethyl-4-piperidyl)ureido]-n-hexane
4-(3-phenylureido)-2,6-diethyl-2,3,6-trimethylpiperidine-1-oxyl
4-butylamino-2,6-diethyl-2,3,6-trimethylpiperidine
4-octylamino-2,6-diethyl-2,3,6-trimethylpiperidine
4-dodecylamino-2,6-diethyl-2,3,6-trimethylpiperidine
4-(N-butylbenzamido)-2,6-diethyl-2,3,6-trimethylpiperidine
4-(N-octylacetamido)-2,6-diethyl-2,3,6-trimethylpiperidine
4-(N-octylbenzamido)-2,6-diethyl-2,3,6-trimethylpiperidine
4-(N-dodecylacetamido)-2,6-diethyl-2,3,6-trimethylpiperidine
4-(N-dodecylbenzamido)-2,6-diethyl-2,3,6-trimethylpiperidine
N,N'-bis-(2,6-diethyl-2,3,6-trimethyl-4-piperidyl)-N,N'-dibutyloxalamide
N,N'-bis-(2,6-diethyl-2,3,6-trimethyl-4-piperidyl)-N,N'-dioctyloxalamide
N,N'-bis-(2,6-diethyl-2,3,6-trimethyl-4-piperidyl)-N,N'-didodecyloxalamide
N,N'-bis-(2,6-diethyl-2,3,6-trimethyl-4-piperidyl)-N,N'-dibutyladipamide
N,N'-bis-(2,6-diethyl-2,3,6-trimethyl-4-piperidyl)-N,N'-dioctylsebacamide
N,N'-bis-(2,6-diethyl-2,3,6-trimethyl-4-piperidyl)-N,N'-dibutylterephthalamide
N,N'-bis-(2,6-diethyl-2,3,6-trimethyl-4-piperidyl)-N,N'-dioctylisophthalamide
1,3-bis-(2,6-diethyl-2,3,6-trimethyl-4-piperidyl)-1,3-dibutylurea 1,3-bis-(2,6-diethyl-2,3,6-trimethyl-4-piperidyl)-1,3-dioctylurea 1,3-bis-(2,6-diethyl-2,3,6-trimethyl-4-piperidyl)-1,3-didodecylurea N,N'-bis-(2,6-diethyl-2,3,6-trimethyl-4-piperidyl)-ethylenediamine N,N'-bis-(2,6-diethyl-2,3,6-trimethyl-4-piperidyl)-hexamethylenediamine N,N'-bis-(2,6-diethyl-2,3,6-trimethyl-4-piperidyl)-N,N'-diacetylethylenediamine N,N'-bis-(2,6-diethyl-2,3,6-trimethyl-4-piperidyl)-N,N'-dibenzoylethylenediamine N,N'-bis-(2,6-diethyl-2,3,6-trimethyl-4-piperidyl)-N,N'-diacetylhexamethylenediamine N,N'-bis-(2,6-diethyl-2,3,6-trimethyl-4-piperidyl)-N,N'-dibenzoyl-hexamethylenediamine 2,4,6-tris(2,6-diethyl-2,3,6-trimethylpiperidinyl-4-amino)-1,3,5-triazine 2,4,6-tris(2,6-diethyl-1,2,3,6-tetramethylpiperidyl-4-amino)-1,3,5-triazine 2,4,6-tris(2,6-diethyl-2,3,6-trimethyl-1-oxylpiperidyl-4-amino)-1,3,5-triazine 1-acetyl-2,6-diethyl-2,3,6-trimethyl-4-acetamidopiperidine 1-acryloyl-2,6-diethyl-2,3,6-trimethyl-4-acrylamidopiperidine 1-crotonyl-2,6-diethyl-2,3,6-trimethyl-4-crotonamidopiperidine 1-acetyl-2,6-diethyl-2,3,6-trimethyl-4-benzamidopiperidine 1-capryloyl-2,6-diethyl-2,3,6-trimethyl-4-benzamidopiperidine 1-lauroyl-2,6-diethyl-2,3,6-trimethyl-4-benzamidopiperidine N,N'-bis(1-acetyl-2,6-diethyl-2,3,6-trimethyl-4-piperidyl)-oxalamide 4-ethoxycarbonamido-2,6-diethyl-2,3,6-trimethyl-piperidine 4-benzyloxycarbonamido-2,6-diethyl-2,3,6-trimethyl-piperidine 4-(4-tert.-butylbenzamido)-2,6-diethyl-2,3,6-trimethylpiperidine 4-(3,5-di-tert-butyl-4-hydroxybenzamido)-2,6-diethyl-2,3,6-trimethylpiperidine 4-[β-(3,5-di-tert-butyl-4-hydroxyphenyl)-propionamido]-2,6-diethyl-2,3,6-trimethylpiperidine.

The 4-aminopiperidine derivatives of formula I can be prepared in different ways using types of reactions which are generally known for the syntheses of amines and amine derivatives. Depending on the type of compounds of formula I an appropriate type of reaction has to be chosen as it is exemplified by the following not limitative selection of possible methods for preparation:

(1) Compounds of formula I wherein $R^7$ and Y are hydrogen or Y is H and $R^7$ is alkyl, cycloalkyl or aralkyl can be synthesised by catalytic hydrogenation of the corresponding 4-oxo-piperidine (II) in the presence of ammonia or a primary amine

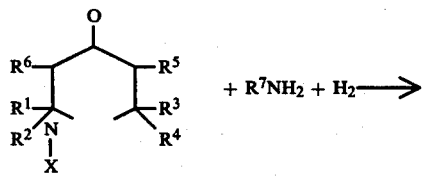

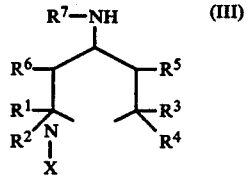

Catalysts are e.g. Raney nickel, palladium on charcoal or platinum oxide. The hydrogenation may preferably carried out in organic solvents e.g., in methanol, ethanol or dioxane.

The 4-oxopiperidines of formula II can be prepared by reacting an aliphatic ketone, this being a higher homologue of acetone, with ammonia. For example 2,3,6-trimethyl-2,6-diethyl-4-oxopiperidine is obtained from methyl ethyl ketone and ammonia as is described by W. Traube in Chem. Berichte 41 (1908), 777.

Another method of synthesis is the hydrolysis of alkylsubstituted tetrahydropyrimidines in the presence of acidic catalysts, for example analogously to the process of U.S. Pat. No. 3,513,170.

Compounds of formula II having different substituents in 2- and 6-position are obtainable by first reacting a ketone $R^1$—CO—$R^2$ with ammonia and hydrolysing the formed pyrimidine derivative resulting in formation of an amino ketone $$R_1-\underset{\underset{NH_2}{|}}{\overset{\overset{R^2}{|}}{C}}-\overset{\overset{R^6}{|}}{CH}-CO-CH_2R^5$$

as is described in Helvet. Chim. Acta 30, (1947), 1114. In a second step this aminoketone is reacted with ammonia and a second ketone $R^3$—CO—$R^4$ resulting in a pyrimidine derivative as is described in Monatsh. Chemie 88 (1957), 464. From this the piperidone derivatives II can be obtained by hydrolysis.

Such and similar methods of preparing alkylated 4-piperidones are further described in German laid open patent applications Nos. 2 429 745, 2 429 746, 2 429 935, 2 429 936, 2 429 937.

(2) Compounds of formula I wherein Y is an acyl residue —$COR^{13}$, —COCO— or —CO—$R^{18}$—CO— may be prepared by acylation of III by means of the corresponding carboxylic or dicarboxylic acids, their anhydrides, their esters of their halogenides according to the usual acylation procedures for primary or secondary amines.

(3) Compounds of formula I wherein Y is a carbamoyl group —CO—NH—$R^{15}$ or —CO—NH—$R^{19}$—N-H—CO— can be synthesized from the amines of formula III by reaction with isocyanates $R^{15}$—NCO and diisocyanates OCN—$R^{19}$—NCO respectively.

(4) Compounds of formula I wherein n is 2 and Y is —CO— or wherein n=1 and Y is —CO—$NH_2$ may be prepared by reaction of amines of formula III with urea or with alkyl carbaminates.

(5) Compounds of formula I wherein Y is a carbamoyl group —CO—N($R^{14}$)($R^{15}$) and both $R^{14}$ and $R^{15}$ are hydrocarbon residues or form a ring together with the N can be prepared from the amines III by reaction with chlorocarbamates of the formula Cl—CO—N($R^{14}$)($R^{15}$).

(6) When Y is a sulfonyl group $-SO_2-R^{16}$ the compounds of formula I may be prepared from the amines III by reacting them with a sulfonic acid chloride, for example with p-toluene-sulfonyl chloride.

(7) Compounds of formula I wherein $R^7$ or Y is $-CO-R^{12}-COOH$ can be prepared from the amines III by reaction with cyclic dicarboxylic anhydrides, e.g. with maleic, succinic or phthalic anhydride. If the compounds thus obtained are further reacted with a dehydrating agent, such as acetic anhydride, compounds of formula I are obtained wherein Y and $R^7$ together with the N-atom form a cyclic imide ring.

(8) The metal salts wherein Y is $-CO-R^{12}-COOMe$ are obtainable from the free carboxylic acids by neutralisation e.g. with an appropriate metal carbonate or hydroxide.

(9) Compounds of formula I wherein Y is a triazinyl, a triazinediyl or a triazinetriyl residue can be synthesized from the amines III by reaction with optionally substituted cyanuric mono-, di- or trichlorides.

(10) Compounds of formula I wherein X is a hydrocarbon residue can be synthesized from the compounds of formula I wherein X is hydrogen by conventional substitution reactions, for example by reaction with dimethyl sulfate, with allyl chloride or with benzyl bromide. Analogously, the nitroxyls (where in formula I X is oxyl) can be obtained from the compounds with X=H by reaction with percarboxylic acids, for example with 3-chloroperbenzoic acid, or with hydrogen peroxide in the presence of catalysts, for example in the presence of sodium tungstate. Alternatively, the N-substitution may be performed with the piperidones of formula II, followed by amination and by the other reactions already mentioned.

(11) Compounds where X is

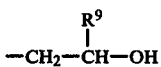

are obtainable from the compounds where X is H by reaction with alkylene oxides such as ethylene oxide, propylene oxide or styrene oxide. If epichlorohydrine is used as alkylene oxide there is obtained a chlorohydrine compound which can be converted to the N-glycidyl compound by alkaline treatment.

(12) Compounds where X is an acyl group may be obtained from the corresponding NH-compounds by acylation with carboxylic acid chlorides, esters of anhydrides. If n is 1 the reaction (12) may be combined with reaction (2) to achieve simultaneous acylation at the ring nitrogen as well as at the amino group in 4-position.

(13) Acid addition salts of the compounds of formula I may be prepared by neutralising the piperidine derivative with the appropriate acids, preferably in an organic solvent or its mixture with water. The formation of a salt is not possible if X and Y are acyl groups or if Y is $-CO-R^{12}-COMe$.

(14) Compounds of formula I, where n is 2, Y is a divalent hydrocarbon residue as defined and $R^7$ is hydrogen, are obtainable from the 4-oxopiperidines of formula II by catalytic hydrogenation in the presence of an equivalent amount of the appropriate diamine. From these products the corresponding acyl derivatives can be prepared, where $R^7$ is $-CO-R^{11}$, by reaction with $R^{11}COCl$ or $(R^{11}CO)_2O$.

In accordance with the invention, it has now been discovered that the 4-aminopiperidine derivatives of formula I and acid addition salts thereof can effectively stabilize a wide range of organic polymers against light-induced deterioration with superior compatibility with polymer substrates. Polymers which can be stabilized in this way include:

1. Polymers of mono- and diolefins, for example polyethylene which can optionally crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene or polypropylene and polyisobutylene.

3. Copolymers of mono- and diolefins, for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene.

4. Polystyrene.

5. Copolymers of styrene and of α-methylstyrene, for example styrene/butadiene copolymers, styrene/acrylonitrile copolymers, styrene/acrylonitrile/methylacrylate copolymers; high impact strength mixtures of styrenecopolymers and other polymers, such as polyacrylates or diene-polymers or ethylene-propylene-diene terpolymers; block copolymers of styrene such as styrene/butadiene/styrene, styrene/isoprene/styrene or styrene/ethylene-butylene/styrene.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, such as polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide, polypropylene oxide or polyisobutylene oxide.

11. Polyacetals, for example polyoxymethylene, as well as polyoxymethylenes which contain for example ethylene oxide as comonomer.

12. Polyphenylene oxides.

13. Polyurethanes and polyureas.

14. Polycarbonates.

15. Polysulphones.

16. Polyamides and copolyamides which are derived from diamines and dicarboxylic acids and/or from aminocarboxylic acids or the corresponding lactames, for example polyamide 6, polyamide 6/6, polyamide 6/10, polyamide 11, polyamide 12.

17. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

18. Cross-linked polymers which are derived from aldehydes on the one hand and from phenols, ureas and melamines on the other, for example phenol/formaldehyde, urea/formaldehyde and melamine/formaldehyde resins.

19. Alkyd resins, for example glycerol/phthalic acid resins and mixtures thereof with melamine/formaldehyde resins.

20. Unsaturated polyester resins which are derived from copolyesters of saturated and unsaturated dicarboxylic acids with polyhydric alcohols as well as from vinyl compounds as cross-linking agents.

21. Cross-linked epoxide resins, derived from polyepoxides, e.g. from bis-glycidyl-ethers or from cycloaliphatic diepoxides.

22. Natural polymers, for example cellulose, rubber, proteins as well as the chemically modified homologous derivatives thereof, for example cellulose acetates, cellulose propionates and cellulose butyrates and the cellulose ethers, for example methyl cellulose.

From these the polymers of groups 1–6, 13 and 16 are of particular interest as the application of the stabilizers according to the invention has an outstanding effect on these polymers. Particularly preferred polymers are polyolefins, styrene homo- and copolymers, polyurethanes and polyamides.

The stabilizer compounds of formula I are added to the polymers in an amount of from 0.01 to 5.0% by weight, based on the weight of the polymer. Preferably they are added in an amount of from 0.02 to 1.0 and most preferably from 0.05 to 0.5% by weight.

The stabilizer of formula I may readily be incorporated into the organic polymers by conventional techniques, at any convenient stage prior to the manufacture of shaped articles therefrom. For example, the stabilizer may be mixed with the polymer in dry powder form, or a solution or a suspension of the stabilizer may be mixed with a solution or suspension of the polymer.

The stabilized polymer compositions of the invention may optionally also contain other known stabilizers or other additives usually known in plastics technology, such as the additives listed in British Pat. No. 1 401 924, pages 11 to 13.

Synergistic effects may appear in using such known additives in combination with the stabilizers of formula I. This is especially true with other light-stabilizers and with organic phosphites.

Of particular importance is the combination of the light-stabilizers of formula I with antioxidants, especially for the stabilisation of polyolefins.

The invention is further illustrated by the following Examples in which all parts and percentages are by weight.

EXAMPLE 1

197.3 g of 2,6-diethyl-2,3,6-trimethylpiperidin-4-one are dissolved in 1.5 liters of methanol which is saturated with ammonia. This solution is hydrogenated in a 3 liter-autoclave at a hydrogen pressure of 100 bar in the presence of 30 g of Raney nickel. After 24 hours, the solution is filtered and the solvent evaporated. The residue is distilled in vacuo yielding 162 g 2,6-diethyl-2,3,6-trimethyl-4-aminopiperidine (compound no. 1) distilling at 133°–35° C. at 23 mm Hg. Using a methanolic solution of methylamine, n-butylamine, n-hexylamine, n-dodecylamine, benzylamine and 2-aminoethanol, respectively, instead of the ammonia solution while otherwise following the procedure described above, there are obtained:

2,6-diethyl-2,3,6-trimethyl-4-methylaminopiperidine (no. 2) b.p. 132°–35° C. at 21 mm Hg, 2,6-diethyl-2,3,6-trimethyl-4-n-butylaminopiperidine (no. 3) b.p. 161°–65° C. at 20 mm Hg, 2,6-diethyl-2,3,6-trimethyl-4-n-hexylaminopiperidine (no. 4) b.p. 173°–76° C. at 20 mm Hg, 2,6-diethyl-2,3,6-trimethyl-4-n-dodecylaminopiperidine (no. 5) b.p. 160°–65° C. at 0.1 mm Hg, 2,6-diethyl-2,3,6-trimethyl-4-benzylaminopiperidine (no. 6) b.p. 126°–28° C. at 0.1 mm Hg.

2,6-diethyl-2,3,6-trimethyl-4(2-hydroxy-ethyl)-aminopiperidine, (no. 6a) b.p. 175°–180° C. at 15 mm Hg.

The 2,6-diethyl-2,3,6-trimethyl-4-piperidone used as a starting material was obtained as follows:

19.6 g of 2,4,6-triethyl-2,6-dimethyl-1,2,5,6-tetrahydropyrimidine and 0.4 g of ammonium bromide were added to 200 ml of methanol. To the mixture were added dropwise 10 g of 37% hydrochloric acid at 10° C., with stirring. After completion of the addition the whole was stirred at room temperature for 4 hours and then there were added further 20 ml of 18% hydrochloric acid. The mixture was then heated at 30°–40° C. for 7 hours and allowed to stand overnight at room temperature. The mixture was made alkaline with 40% aqueous potassium carbonate solution and after methanol was evaporated under reduced pressure the mixture was extracted with ether. The ether solution was dried over potassium carbonate and the ether was removed. The residue was subjected to distillation under reduced pressure to give 15.1 g of the desired compound as an oil boiling at 91°–93° C./2.0 mm Hg.

EXAMPLE 2

197.3 g of 2,6-diethyl-2,3,6-trimethylpiperidine-4-one and 30.0 g of ethylenediamine are dissolved in one liter of methanol. 10 g of a platin-carbon catalyst (5% b.w. Pt) are added, and the solution is hydrogenated at 30°–35° C. and normal pressure. Hydrogenation is completed after 106 hours. The catalyst is filtered off, the solvent is evaporated in vacuo, and the oily residue is purified by molecular distillation at 150° C. and 0.005 mm Hg. N,N'-Bis-(2,6-diethyl-2,3,6-trimethyl-4-piperidyl)-ethylenediamine (compound no. 7) is obtained as a practically colourless oil. If, instead of 30.0 g of ethylenediamine an equivalent amount of 1,6-hexamethylenediamine is used and otherwise the procedure described above is followed, after molecular distillation at 180° C. and 0.002 mm Hg. N,N'-Bis-(2,6-diethyl-2,3,6-trimethyl-4-piperidyl)-hexamethylene-1,6-diamine (compound no. 8) is obtained in the form of a thick colourless oil.

EXAMPLE 3

19.8 g of 2,6-diethyl-2,3,6-trimethyl-4-aminopiperidine are dissolved in 100 ml toluene. To this solution 14 g benzoyl chloride are dropped with stirring at room temperature within 45 minutes. The reaction mixture is warmed to about 80° C. and the stirring is continued at this temperature for further 3 hours. After cooling to room temperature the toluene solution is washed with 200 ml 2 n sodium hydroxide solution, dried over Na$_2$-

SO₄ and concentrated by evaporation to about half the volume. Hexane is added until the solution becomes turbid. On standing the product crystallizes. After crystallization from toluene/hexane the resulting 2,6-diethyl-2,3,6-trimethyl-4-benzamidopiperidine (no. 9) melts at 160° C. Carrying out the same procedure but using instead of benzoyl chloride the corresponding stoichiometric amount of acetyl chloride, capryloyl chloride, adipoyldichloride, sebacoyldichloride, terephthaloyl dichloride, methane sulfochloride or p-toluene sulfochloride there are obtained:

2,6-diethyl-2,3,6-trimethyl-4-acetamidopiperidine (no. 10), b.p.$_{0.005}$ 105° C.

2,6-diethyl-2,3,6-trimethyl-4-caprylamidopiperidine (no. 11) b.p.$_{0.005}$ 115° C.

N,N'-bis(2,6-diethyl-2,3,6-trimethyl-4-piperidyl)adipamide (no. 12) m.p. 191° C.

N,N'-bis(2,6-diethyl-2,3,6-trimethyl-4-piperidyl)sebacamide (no. 13) (yellow resin)

N,N'-bis(2,6-diethyl-2,3,6-trimethyl-4-piperidyl)terephthalamide (no. 14) m.p. 272° C.

2,6-diethyl-2,3,6-trimethyl-4-methanesulfonamidopiperidine (no. 15) b.p.$_{0.005}$ 110° C.

2,6-diethyl-2,3,6-trimethyl-4-p-toluenesulfonamidopiperidine (no. 16), m.p. 92° C.

EXAMPLE 4

14.6 g diethyl oxalate are dissolved in 100 ml dry methanol. 39.6 g 2,6-diethyl-2,3,6-trimethyl-4-aminopiperidine are dropped into this solution within about 15 minutes. The reaction mixture is stirred 12 hours under heating to reflux. After distilling off the solvent the residue crystallizes on cooling. After recrystallisation from acetonitrile the obtained N,N'-bis-(2,6-diethyl-2,3,6-trimethyl-4-piperidyl)oxalamide (no. 17) melts at 142° C.

EXAMPLE 5

39.7 g 2,6-diethyl-2,3,6-trimethyl-4-methylaminopiperidine are dissolved in 100 ml toluene. 28.1 g benzoyl chloride are added to this solution within 45 minutes from a dropping funnel. The reaction is exothermic and the temperature rises to 54° C. The reaction mixture is stirred 24 hours without cooling or heating. Afterwards 200 ml toluene are added and the toluene solution is washed with 200 ml 2 n sodium hydroxide solution, dried over sodium sulfate and evaporated. The residue is purified by molecular distillation. The 2,6-diethyl-2,3,6-trimethyl-4-(N-methylbenzamido)-piperidine (no. 18) distills at 125° C. and 0.005 mm Hg. Carrying out the same procedure as described above but using instead of benzoyl chloride the corresponding stoichiometric amount of acetyl chloride or acryloyl chloride, there are obtained:

2,6-diethyl-2,3,6-trimethyl-4-(N-methylacetamido)-piperidine (no. 19) b.p.$_{0.3}$ 85° C.

2,6-diethyl-2,3,6-trimethyl-4-(N-methylacrylamido)-piperidine (no. 20) b.p.$_{0.001}$ 100° C.

EXAMPLE 6

84.4 g of N,N'-bis-(2,6-diethyl-2,3,6-trimethyl-4-piperidyl)-ethylenediamine (compound no. 7) are carefully added to 250 ml of acetic anhydride and then stirred at 100° C. for 5 hours. Excess anhydride is distilled off under vacuum, and the residue is dissolved in water. The resultant aqueous solution is adjusted to pH 11-12 by careful addition of concentrated sodium hydroxide solution, and then extracted with 300 ml of toluene. The toluene solution is washed with water, dried over sodium sulfate and evaporated to dryness. Crystallization of the residue from acetonitrile yields N,N'-diacetyl-N,N'-bis(2,6-diethyl-2,3,6-trimethyl-4-piperidyl)-ethylenediamine (compound no. 21); m.p. 173°-175° C. If, intead of 84.4 g of N,N'-bis-(2,6-diethyl-2,3,6-trimethyl-4-piperidyl)-ethylenediamine equivalent amounts of N,N'-bis-(2,6-diethyl-2,3,6-trimethyl-4-piperidyl)-hexamethylene-1,6-diamine (compound no. 8) are used and otherwise the procedure described above is followed, N,N'-diacetyl-N,N'-bis-(2,6-diethyl-2,3,6-trimethyl-4-piperidyl)-hexamethylene-1,6-diamine is obtained (compound no. 22) in the form of a thick, light-brown resin (molecular distillation at 150° and 0.002 mm Hg).

EXAMPLE 7

6 g of 2,6-diethyl-2,3,6-trimethyl-4-benzamidopiperidine (no. 9), 5,6 g of methyliodide, 3 g K₂CO₃ and 100 ml dimethyl formamide are stirred for 48 hours at 45° C. 10 ml of water are added to the reaction mixture and the formed precipitate is isolated by filtration, washed with water and dried. After a recrystallisation from acetonitrile the obtained 2,6-diethyl-1,2,3,6-tetramethyl-4-benzamidopiperidine (no. 23) melts at 183° C. If, instead of 6 g of 2,6-diethyl-2,3,6-trimethyl-4-benzamidopiperidine an equivalent amount of N,N'-diacetyl-N,N'-bis(2,6-diethyl-2,3,6-trimethyl-4-piperidyl)-hexamethylene-1,6-diamine (compound no. 22) is used and otherwise the procedure described above is followed, N,N'-diacetyl-N,N'-bis-(2,6-diethyl-1,2,3,6-tetramethyl-4-piperidyl)-hexamethylene-1,6-diamine (compound no. 24) is obtained in the form of a viscous light brown resin (molecular distillation at 160°-165° C. and 0.001 mm Hg).

EXAMPLE 8

12 g of 2,6-diethyl-2,3,6-trimethyl-4-benzamidopiperidine (no. 9) and 100 ml acetic anhydride are stirred for 48 hours at 80° C. The reaction mixture is evaporated to dryness in vacuo. The residue is washed with about 200 ml water, dried and recrystallized from toluene/hexane. The obtained 1-acetyl-2,6-diethyl-2,3,6-trimethyl-4-benzamidopiperidine (no. 25) melts at 169° C. If, instead of 12 g of 2,6-diethyl-2,3,6-trimethyl-4-benzamidopiperidine an equivalent amount of N,N'-bis-(2,6-diethyl-2,3,6-trimethyl-4-piperidyl)-oxalamide (compound no. 17) is used and otherwise the procedure described above is followed, N,N'-bis-(1-acetyl-2,6-diethyl-2,3,6-trimethyl-4-piperidyl)-oxalamide is obtained (compound no. 26); m.p. 164° C.

EXAMPLE 9

49.5 g of 2,6-diethyl-2,3,6-trimethyl-4-amino-piperidine (compound no. 1), 71.5 g of acetic acid anhydride and 70.5 g finely powdered, calcined potash are 24 hours stirred in 350 ml of xylene at a temperature of 130°-135° C. At the begin of the reaction a violent evolution of carbon dioxide sets in which gradually ceases during the stirring period. After finished reaction the slurry of potassium acetate is filtered off and the xylene solution is evaporated under reduced pressure. The remaining brownish crystalline mass is recrystallized twice from toluene. The so purified 1-acetyl-2,6-diethyl-2,3,6-trimethyl-4-acetaminopiperidine (compound no. 26a) melts at 151° C.

EXAMPLE 10

30.3 g of 2,6-diethyl-2,3,6-trimethyl-4-benzamidopiperidine (compound no. 9), 200 ml of methanol and 2 ml of concentrated hydrochloric acid are introduced into an autoclave. About 9 g of ethyleneoxide are added, and the contents of the autoclave are heated to 130° C. for 30 hours. After cooling, the contents of the autoclave are purified by filtration, and the methanol is evaporated. Crystallization of the residue from toluene yields 1-β-hydroxyethyl-2,6-diethyl-2,3,6-trimethyl-4-benzamidopiperidine (compound no. 27); m.p. 212°–214° C. If, instead of 30.3 g of 2,6-diethyl-2,3,6-trimethyl-4-benzamidopiperidine an equimolar amount of N,N'-diacetyl-N,N'-bis-(2,6-diethyl-2,3,6-trimethyl-4-piperidyl)-hexamethylene-1,6-diamine (compound no. 22), 12 g instead of 9 g of ethyleneoxide are used and otherwise the procedure described above is followed, N,N'-diacetyl-N,N'-bis-(1-β-hydroxyethyl-2,6-diethyl-2,3,6-trimethyl-4-piperidyl)-hexamethylene-1,6-diamine (compound no. 28) is obtained as a yellowish viscous resin.

EXAMPLE 11

29.8 g of 2,6-diethyl-2,3,6-trimethyl-4-aminopiperidine and 9 g urea are heated 20 hours to 130° C. At the beginning of the reaction the mixture can be stirred, lateron it is solidifying more and more. The product is recrystallised from toluene, the resulting 2,6-diethyl-2,3,6-trimethyl-4-ureidopiperidine (no. 29) melts at 176° C.

EXAMPLE 12

39.7 g of 2,6-diethyl-2,3,6-trimethyl-4-aminopiperidine are reacted with 9 g of ethyl carbaminate during 8 hours at 155° C. The crude reaction product is recrystallized twice from toluene. The resulting 1,3-bis-(2,6-diethyl-2,3,6-trimethyl-4-piperidyl)-urea (no. 30) does not melt up to 280° C. where it begins to sublimate.

EXAMPLE 13

29.8 g of 2,6-diethyl-2,3,6-trimethyl-4-aminopiperidine are dissolved in 200 ml dry toluene. 17.9 g of phenyl isocyanate are dropped to the solution within about 30 minutes whereupon an exothermic reaction sets in. The mixture is stirred for further 12 hours, during this period the product crystallizes. After recrystallisation the 4-(3-phenylureido)-2,6-diethyl-2,3,6-trimethyl-piperidine (no. 31) melts at 187° C. Carrying out the same procedure using instead of 17.9 g of phenyl isocyanate the equivalent amounts of ethyl isocyanate, octadecyl isocyanate, hexamethylene diisocyanate and toluene-2,4-diisocyanate, respectively, there are obtained:

4-(3-ethylureido)-2,6-diethyl-2,3,6-trimethylpiperidine (no. 32) as viscous, yellow mass, 4-(3-octadecylureido)-2,6-diethyl-2,3,6-trimethylpiperidine (no. 33), melting at about 40° C., 1,6-bis[3-(2,6-diethyl-2,3,6-trimethyl-4-piperidyl)-ureido] hexane (no. 34), melting at 246° C.

1,1'-bis(2,6-diethyl-2,3,6-trimethyl-4-piperidyl)-3,3'-(2,4-toluylene)diurea (no. 35), m.p. >270° C.

EXAMPLE 14

96.7 g of 2,6-diethyl-2,3,6-trimethyl-4-n-butyl-aminopiperidine (compound no. 3) are dissolved in 300 ml of toluene. In about 1 hour 64.0 g of hexamethylenediisocyanate are added dropwise, and the reaction mixture is stirred for 5 hours at 50° C. After cooling to 10°–12° C., the precipitate is filtered off and recrystallized from toluene. 1,6-Bis-[3-n-butyl-3-(2,6-diethyl-2,3,6-trimethyl-4-piperidyl)-ureido]hexane is obtained (compound no. 36); m.p. 146° C.

EXAMPLE 15

14.4 g of 2,6-diethyl-2,3,6-trimethyl-4-benzylaminopiperidine (compound no. 6) are stirred in 50 ml of acetic anhydride at 50° C. for 24 hours. Excess acetic anhydride is distilled off under vacuum, the residue is taken up in 100 ml of toluene and extracted with 100 ml of 2 n sodium hydroxide solution. The toluene solution is dried over sodium sulfate and evaporated. Molecular distillation of the residue at 130° C. and 0.003 mm Hg yields 2,6-diethyl-2,3,6-trimethyl-4-acetylbenzylaminopipyridine (compound no. 37) as a yellowish viscous oil.

EXAMPLE 16

14.4 g of 2,6-diethyl-2,3,6-trimethyl-4-benzylaminopiperidine (compound no. 6) are dissolved in 50 ml of toluene. 6.0 g of phenylisocyanate are added dropwise at room temperature and in the course of about 15 minutes, and the reaction mixture is then stirred for 5 hours at 80° C. After evaporation of the solution under vacuo the residue is recrystallized from hexane. 4-N-Benzyl-4-(3-phenylureido)-2,6-diethyl-2,3,6-trimethylpiperidine (compound no. 38) is obtained; m.p. 116°–117° C.

EXAMPLE 17

7.9 g of 4-(3-phenylureido)-2,6-diethyl-2,3,6-trimethylpiperidine (no. 31) are dissolved in 30 ml of methylene chloride. Asolution of 12.2 g m-chloroperbenzoic acid in 100 ml methylene chloride is added to the former solution and the mixture is stirred for 12 hours. The precipitated m-chlorobenzoic acid is filtered off, the filtered solution is washed twice with 100 ml 2 n sodium hydroxide, dried over sodium sulfate and the solvent evaporated. The crude residue is crystallized from toluene yielding 4-(3-phenylureido)-2,6-diethyl-2,3,6-trimethylpiperidine-1-oxyl (no. 39) melting at 176° C.

EXAMPLE 18

18.4 g of cyanuric chloride are suspended in 200 ml of xylene. At room temperature 65.5 g of 2,6-diethyl-2,3,6-trimethyl-4-aminopiperidine are added dropwise during 30 minutes. The reaction is continued for 2 hours at 35°–40° C. Within about 15 minutes a solution of 13.2 g of sodium hydroxide in 50 ml of water is added dropwise to the reaction mixture, and the reaction mixture is heated for 8 hours at 85°–90° C. Thereafter the water is removed by azeotropic distillation, and the xylene solution is stirred for 16 hours at 130° C. The reaction mixture is extracted three times with 100 ml of water, the xylene solution is dried over sodium sulfate and evaporated under vacuum. The residue is recrystallized from acetonitrile. 2,4,6-Tris-(2,6-diethyl-2,3,6-trimethyl-piperidyl-4-amino)-1,3,6-triazine (compound no. 40) is obtained; m.p. 115°–120° C. If, instead of 65.5 g of 2,6-diethyl-2,3,6-trimethyl-4-aminopiperidine an equivalent amount of 2,6-diethyl-2,3,6-trimethyl-4-methylaminopiperidine is used and otherwise the procedure described above is followed, 2,4,6-tris-(2,6-diethyl-2,3,6-trimethylpiperidyl-4-methylamino)-1,3,5-triazine (compound No. 41) is obtained; m.p. 132°–138° C.

EXAMPLE 19

49.0 g of maleic anhydride in 300 ml of dioxane are heated to 80° C. At this temperature 99.2 g of 2,6-diethyl-2,3,6-trimethyl-4-aminopiperidine are added dropwise in the course of 30 minutes. After a short time a light brown precipitate is formed. The reaction is continued for 1 hour at reflux temperature. The reaction mixture is then cooled to room temperature, and the precipitate is filtered off. The resultant residue is dissolved in 500 ml of warm water. A brownish solution is formed which is discoloured with active carbon, and then evaporated to dryness under vacuo. The solid residue is suspended in about 200 ml of warm ethanol, the suspension is cooled to room temperature, filtered and dried. 2,6-Diethyl-2,3,6-trimethyl-4-$\beta$-carboxy-acrylamidopiperidine (compound no. 42) is obtained: m.p. >250° C. If, instead of 49.0 g of maleic anhydride an equivalent amount of phthalic anhydride is used and otherwise the procedure described above if followed, 2,6-diethyl-2,3,6-trimethyl-4-o-carboxybenzamidopiperidine (compound no. 43) is obtained; m.p. 196°–197° C.

EXAMPLE 20

20 g of 2,6-diethyl-2,3,6-trimethyl-4-$\beta$-carboxy-acrylamidopiperidine (compound no. 42) are stirred for 15 hours at 70° C. in 100 ml of acetic anhydride and 100 ml of toluene. The reaction mixture is evaporated to dryness under vacuum, the residue is added to 200 ml of 2 n sodium hydroxide solution and extracted three times with 50 ml of toluene. The toluene solution is evaporated to dryness under vacuum, and the residue is subjected to molecular distillation at 85° C. and 0.003 mm Hg. 2,6-Diethyl-2,3,6-trimethyl-4-maleimidopiperidine (compound no. 44) is obtained as a thick slightly yellowish oil.

If, instead of 20 g of 2,6-diethyl-2,3,6-trimethyl-4-$\beta$-carboxy-acrylamidopiperidine an equivalent amount of 2,6-diethyl-2,3,6-trimethyl-4-$\beta$-carboxy-propionamidopiperidine (compound no. 45, obtained by reacting succinic acid anhydride with 2,6-diethyl-2,3,6-trimethyl-4-aminopiperidine in a manner analogous to that described in Example 19) or 2,6-diethyl-2,3,6-trimethyl-4-o-carboxy-benzamidopiperidine (compound no. 43) is used and otherwise the procedure described above is followed, 2,6-diethyl-2,3,6-trimethyl-4-succinimodopiperidine (compound no. 46) as a yellow oil (molecular distillation at 100° C. and 0.003 mm Hg) and 2,6-diethyl-2,3,6-trimethyl-4-phthalimidopiperidine (compound no. 47) as a yellow resin are obtained.

EXAMPLE 21

20 g of 2,6-diethyl-2,3,6-trimethyl-4-benzamidopiperidine (compound no. 9), 12.5 g of benzylbromide, 1 g of potassium iodide and 20 g of potassium carbonate are stirred in 200 ml of tetrahydrothiophene dioxide (sulpholane) at 110° C. for 4 days. Thereafter the reaction mixture is diluted with 200 ml of toluene, cooled to room temperature and purified by filtration. The filtrate is washed four times with about 200 ml of water, the toluene phase is dried over sodium sulfate and evaporated under vacuum. Crystallization of the residue from acetic acid ethyl ester yields 1-benzyl-2,6-diethyl-2,3,6-trimethyl-4-benzamidopiperidine (compound no. 48); m.p. 234°–236° C.

If, instead of 12.5 g of benzylbromide an equivalent amount of 1-bromooctane is used and the reaction mixture is stirred for 6 days, the reaction conditions being otherwise the same as described above, after crystallization from acetic acid ethyl ester 1-octyl-2,6-diethyl-2,3,6-trimethyl-4-benzamidopiperidine (compound no. 49) is obtained; m.p. 173°–176° C.

EXAMPLE 22

19.8 g of 2,6-diethyl-2,3,6-trimethyl-4-aminopiperidine and 12 g of triethylamine are dissolved in 100 ml of toluene. At 25° to 30° C., 19.3 g of chloroformic acid octylester are added dropwise to this solution in the course of about 15 minutes. The reaction mixture is then stirred for 24 hours at 60° C. and cooled to 10°–15° C. The precipitated triethylamine hydrochloride is filtered off, and the residue is distilled at 95°–100° C./0.001 mm Hg. 2,6-Diethyl-2,3,6-trimethyl-4-octyloxycarbonamidopiperidine is obtained as a viscous yellowish oil (no. 50).

EXAMPLE 23

100 parts polypropylene powder (Moplen, fibre grade, Montedison Comp.) and 0.2 parts octadecyl $\alpha$-(3,5-di-tert.butyl-4-hydroxyphenyl)-propionate as antioxidant and 0.25 parts of a light-stabiliser listed in Table 1 are homogenised in a Brabender plastograph during 10 minutes at 200° C. The resulting mass is pressed to a 2 to 3 mm thick sheet in a laboratory press. The sheet is hot pressed in a hydraulic press during 6 minutes at 260° C. and a pressure of 12 tons yielding a 0.5 mm thick film which is quenched immediately in cold water. By the same procedure a 0.1 mm film is made from the 0.5 mm film.

Test specimens of 66×44 mm are cut from the film and irradiated in a "Xenotest 150" radiation equipment. The content of carbonyl groups of the irradiated films is periodically controlled by infrared spectroscopy. The increase of carbonyl groups characterized by the infrared extinction at 5.85$\mu$ is a relevant measure for the light-induced deterioration of polypropylene (see L. Balaban et al., J. Polymer Sci., Part C, 22 (1969) 1059–1071) and is, according to experience, accompanied by a gradual loss of the mechanical properties of the polymer. The time to reach a carbonyl extinction of 0.3 at which the control sample is brittle was taken as a measure of the effectiveness of the stabilizers and is indicated in Table 1.

Table 1

| Compound (No. given in Examples 1–12) | Irradiation time (hours) until 0.30 Carbonyl extinction |
|---|---|
| none | 950 |
| No. 9 | 6350 |
| 10 | 7500 |
| 11 | 6140 |
| 12 | 4390 |
| 13 | 4560 |
| 16 | 4450 |
| 17 | 6210 |
| 18 | 6300 |
| 30 | 6830 |
| 31 | 3840 |

EXAMPLE 24

100 parts of granulated polystyrene are dry mixed with 0.25 parts of one of the light-stabilizers listed in Table 2. The mixture is regranulated in an extruder and is injection moulded to give 2 mm thick sheets. The sheets are irradiated for 2000 resp. 3000 hours in a "Xenotest 150" irradiation equipment and their yellowing is determined from the yellowing factor (Y.F.).

$$Y.F. = (\Delta T\,(420) - \Delta T\,(680))/T\,(560) \times 100$$

Therein ΔT denotes the loss in transmission at the wavelengths 420 and 680 mm respectively during the irradiation, and T (560) is the transmission value of the unexposed sample at 560 nm.

Table 2

| Compound No. given in Examples 1-12 | Yellowing Factor | |
| --- | --- | --- |
| | 2000 h | 3000 h |
| none | 15.7 | 34.8 |
| No. 9 | 4.4 | 11.1 |
| 17 | 6.6 | 15.5 |
| 31 | 7.7 | 13.3 |

What we claim is:

1. A compound of the formula

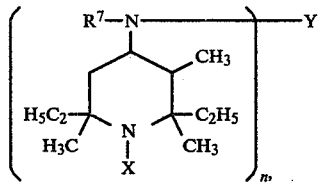

a mixture of isomers thereof, or an acid addition salt thereof wherein n is 1 to 3 X is hydrogen, methyl, benzyl, aliphatic acyl having 1 to 4 carbon atoms or 2-hydroxyethyl, $R^7$ is hydrogen, alkyl having 1 to 12 carbon atoms benzyl, or, if n is 2 and Y is alkylene having 2 to 10 carbon atoms, $R^7$ is hydrogen or acetyl, Y, if n is 1, represents hydrogen, —CH$_2$CH$_2$OH, —CO—$R^{13}$ wherein $R^{13}$ is hydrogen, alkyl having 1 to 7 carbon atoms, alkenyl having 2 or 3 carbon atoms or phenyl, —CONH-$R^{15}$ wherein $R^{15}$ is alkyl having 1 to 18 carbon atoms or phenyl, —SO$_2R^{16}$ wherein $R^{16}$ is methyl, phenyl or pary-methylphenyl, —CO—$R^{1}$$_2$—COOH wherein $R^{12}$ is —CH$_2$CH$_2$—, —CH=CH— or o-phenylene, or Y and $R^7$ together with the N-atom to which they are attached form a succinimide, maleimide or phthalimide ring, if n is 2, Y represents —CO—, —CO—CO—, —CO—$R^{18}$—CO— wherein $R^{18}$ is alkylene having 1 to 8 carbon atoms or phenylene or —CONH—$R^{19}$—NHCO— wherein $R^{19}$ is alkylene having 2 to 6 carbon or tolylene, and if $R^7$ is hydrogen or acetyl, Y may also be alkylene having 2 to 6 carbon atoms, and, if n is 3, Y represents the 1,3,5-triazine-2,4,6-triyl residue.

2. A compound as claimed in claim 1 wherein $R^7$ is hydrogen, alkyl having 1 to 12 carbon atoms or benzyl.

3. A compound as claimed in claim 1 wherein X is hydrogen or methyl.

4. A compound as claimed in claim 1 wherein Y, if n is 1, represents hydrogen, and if n is 2 and $R^7$ is hydrogen or acetyl, Y represents alkylene having 2 to 6 carbon atoms.

5. A compound as claimed in claim 1 which is N,N'-bis-(2,6-diethyl-2,3,6-trimethyl-4-piperidyl)-oxalamide.

6. A compound as claimed in claim 1 which is N,N'-bis(2,6-diethyl-2,3,6-trimethyl-4-piperidyl)-adipamide.

7. A compound as claimed in claim 1 which is N,N'-bis-(2,6-diethyl-2,3,6-trimethyl-4-piperidyl)-hexamethylenediamine.

8. A compound of the formula I

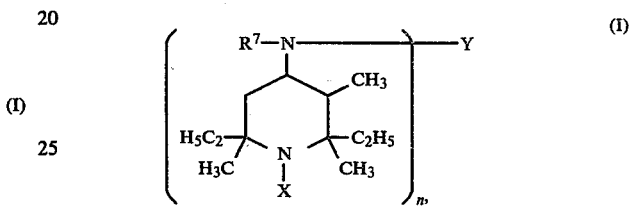

a mixture of isomers thereof, or an acid addition salt thereof wherein X is hydrogen or aliphatic acyl having 1 to 4 carbon atoms, $R^7$ is hydrogen or alkyl having 1-12 carbon atoms, Y, if n is 1, represents hydrogen, —CO-$R^{13}$ wherein $R^{13}$ is hydrogen, alkyl having 1 to 7 carbon atoms or phenyl, or —CONH-$R^{15}$ wherein $R^{15}$ is alkyl having 1-18 carbon atoms or phenyl, and, if n is 2, Y represents —CO—, —CO—CO—, or —CO—$R^{1}$$_8$—CO— wherein $R^{18}$ is alkylene having 1-8 carbon atoms, with the proviso that only one of $R^7$ and Y is hydrogen when n is 1.

9. 4-Dodecylamino-2,6-diethyl-2,3,6-trimethylpiperidine.

10. 4-Amino-2,6-diethyl-2,3,6-trimethylpiperidine.

11. A composition of matter stabilized agains light-induced deterioration comprising an organic polymer, normally subject to deterioration by light, and from 0.01 go 5.0 percent by weight of a compound of formula I as claimed in claim 1, a mixture of isomers thereof or an acid addition salt thereof.

12. A composition as claimed in claim 11 wherein the organic polymer is a polyolefin or a styrene homo- or copolymer.

13. A composition as claimed in claim 11 wherein the organic polymer is a polyurethane or a polyamide.

* * * * *